United States Patent
Nierlich et al.

[11] Patent Number: 5,912,191
[45] Date of Patent: Jun. 15, 1999

[54] PROCESS FOR PREPARING ALKYL TERT-BUTYL ETHERS AND DI-N-BUTENE FROM FIELD BUTANES

[75] Inventors: Franz Nierlich, Marl; Paul Olbrich, Haltern; Wilhelm Droste, Marl; Richard Mueller, Marl; Walter Toetsch, Marl, all of Germany

[73] Assignee: Huels Aktiengesellschaft, Marl, Germany

[21] Appl. No.: 08/899,797

[22] Filed: Jul. 24, 1997

[30] Foreign Application Priority Data

Jul. 24, 1996 [DE] Germany ............... 196 29 905

[51] Int. Cl.⁶ ............... C10L 1/18; C07C 41/06
[52] U.S. Cl. ............... 44/449; 568/697
[58] Field of Search ............... 44/449

[56] References Cited

U.S. PATENT DOCUMENTS

| | | | |
|---|---|---|---|
| 4,252,541 | 2/1981 | Herbstman | 44/449 |
| 4,377,393 | 3/1983 | Schleppinghoff | 44/449 |
| 4,797,133 | 1/1989 | Pujado | 44/449 |
| 4,925,455 | 5/1990 | Harandi et al. | 44/449 |
| 4,975,097 | 12/1990 | Harandi et al. | 44/449 |
| 5,024,679 | 6/1991 | Harandi et al. | 44/449 |
| 5,176,719 | 1/1993 | Harandi et al. | 44/449 |
| 5,210,326 | 5/1993 | Marquez et al. | 568/697 |
| 5,243,090 | 9/1993 | Haag et al. | 568/697 |
| 5,723,687 | 3/1998 | Marchionna et al. | 568/697 |

FOREIGN PATENT DOCUMENTS

| | | |
|---|---|---|
| 0 149 698 | 7/1985 | European Pat. Off. . |
| 0 395 857 | 11/1990 | European Pat. Off. . |

OTHER PUBLICATIONS

S. T. Bakas, et al., AIChE Summer Meeting, pp. 1–32, Aug. 19–22, 1990, "Production of Ethers From Field Butanes and Refinery Streams".

Y. Chauvin, et al., Jahrgang. Heft, vol. 7/8, pp. 309–315, Jul./Aug. 1990, "Upgrading of $C_2$, $C_3$, and $C_4$ Olefins by IFP Dimersol Technology".

R. L. Espinoza, et al., Applied Catalysis, vol. 31, pp. 259–266, Mar. 1987, "Catalytic Oligomerization of Ethene Over Nickel–Exchanged Amorphous Silica–Alumina; Effect of the Nickel Concentration".

H. W. Grote, The Oil and Gas Journal, pp. 73–76, Mar. 31, 1958, "Introducing: Alkar and Butamer".

F. Nierlich, Huels Publication, Clean Fuel Technology, Hydrocarbon Processing, 2 pages, Feb. 1992, "Oligomerize for Better Gasoline".

F. Nierlich, Huels Publication, Oil Gas Refining, 6 pages, Oct. 15–16, 1992, "Recent Developments in Olefin Processing for Cleaner Gasoline".

F. Nierlich, et al., Huels Publication, Erdol & Kohle, Erdgas, 6 pages, Feb. 1992, "Verfahren Zur Selektiven Hydrierung Mehrfach Ungesaettigter Kohlenwasserstoffe in Olefin–Gemischen" (with English Abstract).

F. Nierlich, Erdol & Kohle, Erdgas Petrochemie, AIChE 1987 Summer National Meeting, 4 pages, Aug. 16–19, 1987, "Intgrated Tert. Butyl Alcohol/Di–n–Butenes Production From FCC $C_4$'s".

R.A. Pogliano, et al., Petrochemical Review, pp. 1–22, Mar. 19–21, 1996, "Dehydrogenation–Based Ether Production Adding Value to LPG and Gas Condensate".

Bernhard Scholz, et al., Methyl Tert–Butyl Ether, vol. A 16, pp. 543–550, "Methyl Tert–Butyl Ether".

G. C. Sturtevant, et al., UOP Technology Conference, pp. 2,4,6,8,10,12,14,16 and 18, 1988, "Oleflex Selective Production of Lights Olefins".

K. H. Walter, et al., DGMK–Conference, 34 pages, Nov. 11–12, 1993, "Selective Hydrogenation and Dehydrogenation".

*Primary Examiner*—Ellen M. McAvoy
*Attorney, Agent, or Firm*—Oblon, Spivak, McClelland, Maier & Neustadt, P.C.

[57] ABSTRACT

A process for the coupled production of alkyl tert-butyl ethers and butene oligomers from a mixture containing isobutane and n-butane. The isobutane is converted to the alkyl tert-butyl ether and the n-butane is converted to the oligomers. The ratio of the two reaction products may be controlled by setting the ratio of n-butane to isobutane appropriately by isomerization.

20 Claims, 1 Drawing Sheet

PROCESS FOR PREPARING ALKYL TERT-BUTYL ETHERS AND DI-N-BUTENE FROM FIELD BUTANES

BACKGROUND OF THE INVENTION

1. Field of the Invention

The invention relates to a process for preparing alkyl tert-butyl ethers and butene oligomers from a mixture containing isobutane and n-butane, where the isobutane is converted to the alkyl tert-butyl ether and the n-butane is converted to the oligomers. The ratio of the two reaction products may be controlled by adjusting the ratio of n-butane to isobutane.

2. Description of the Background

Alkyl tert-butyl ethers (RTBE, where R represents alkyl) are used as additives to motor gasoline to increase the octane rating. They are generally prepared by addition of alkanols to isobutene, i.e., etherification. The isobutene may originate from four different sources: steam crackers, propylene oxide plants, petroleum refineries (i.e., FC crackers) and plants for the dehydrogenation of isobutane (cf. R. A. Pogliano et al., Dehydrogenation-Based Ether Production—Adding Value to LPG and Gas Condensate. 1996 Petrochemical Review, DeWift & Company, Houston, Tex.). In the first three sources, the isobutene arises as a constituent of the $C_4$ fraction, that is as a direct byproduct. In the dehydrogenation of isobutane, isobutene is frequently a secondary byproduct of such plants, since the starting material isobutane is likewise obtained as a direct byproduct in steam crackers and petroleum refineries or by isomerization of n-butane, which itself is a byproduct in steam crackers and petroleum refineries. The current world production of RTBE is around 25 million metric ten/year, with an increasing trend. The production of butanes and butenes as byproducts in a particular cracker or a particular petroleum refinery is too small to be able to exploit completely the "economies of scale", which are latent in the RTBE process. Therefore, isobutene and/or isobutane (for dehydrogenation) would have to be collected from crackers and/or refineries, in order to be able to operate an RTBE plant at optimum capacity. Alternatively, sufficient $C_4$ fraction could be collected from such plants and these could be worked up together on site to isobutene and isobutane. However, opposing both variants, and in particular the second, is the fact that the transport of liquid gases is expensive, in part due to the complex safety precautions necessary.

The term dibutene refers to the isomeric mixture which, in addition to higher butene oligomers, is formed by dimerization and/or codimerization of butenes, i.e., of n-butene and/or isobutene, in the oligomerization of butenes. Generally, the term dibutene refers to the dimerization products obtained from a mixture of n-butene and isobutene. The term di-n-butene refers to the dimerization product of n-butene, i.e., 1-butene and/or 2-butene. Significant components of the di-n-butene are 3-methyl-2-heptene, 3,4-dimethyl-2-hexene, and, to a minor extent, n-octenes. Di-isobutene is the isomeric mixture which is formed by dimerization of isobutene. Di-isobutene is more highly branched than dibutene and this, in turn, is more highly branched than di-n-butene.

Dibutene, di-n-butene and di-isobutene are starting materials for preparing isomeric nonanols by hydroformylation and hydrogenation of the $C_9$ aldehydes thus formed. Esters of these nonanols, in particular the phthalic esters, are plasticizers which are prepared in large quantities and are primarily used for poly(vinyl chloride). Nonanols from di-n-butene are linear to a greater extent than nonanols from dibutene, which in turn are less branched than nonanols from di-isobutene. Esters of nonanols from di-n-butene have application advantages over esters from other nonanols and are, therefore, particularly in demand.

n-Butene is obtained for the dimerization, just as is isobutene, from $C_4$ fractions, for example, that arise in steam crackers or FC crackers. The $C_4$ fractions are generally worked up by first separating off 1,3-butadiene by a selective scrubbing, e.g., with N-methylpyrrolidone. Isobutene is a desirable and particularly valuable component of the $C_4$ fraction because it may be chemically reacted, alone or in a mixture with other $C_4$ hydrocarbons, to give sought-after products, e.g., with isobutene to give high-octane isooctane, or with an alkanol to give an RTBE, in particular with methanol to give methyl tert-butyl other (MTBE). After the reaction of the isobutene, the n-butenes and n-butane and isobutane remain behind. However, the proportion of n-butene in the cracked products of the steam crackers or the petroleum refineries is relatively small. In the case of steam crackers it is in the order of magnitude of barely 10 percent by weight, based on the principal target product ethylene. A steam cracker having the respectable capacity of 600,000 metric t/year of ethylene therefore only delivers aroung 60,000 metric t/year of n-butene. Although this amount (and that of the isobutenes) could be increased by dehydrogenating the approximately 15,000 metric t/year of n-butane and isobutane, which arise in addition to the n-butenes, this is not advisable, because dehydrogenation plants require high capital expenditure and are thus uneconomic for such a small capacity.

Isobutene is, as discussed above, a sought-after cracking product and is therefore generally not available for the isomerization to n-butene. The amount of n-butenes which a steam cracker or petroleum refinery produces directly is not sufficient, however, to produce sufficient di-n-butene for a nonanol plant of a high enough capacity that it could compete economically with the existing large-scale plants for preparing important plasticizer alcohols, such as 2-ethylhexanol. Propylene oxide plants are, as already stated even less productive still. n-Butenes would therefore have to be collected from various steam crackers, refineries or propylene oxide plants (or $C_4$ fraction from various sources worked up to n-butene) and the combined n-butene oligomerized in order to cover the dibutene requirement of a sufficiently large economical nonanol plant. However, the transport of liquid gases is expensive and dangerous, as discussed above.

It would therefore be desirable if n-butene and isobutene could be provided at only one site without transport over relatively large distances in amounts as are required in a coupled production for the operation of a large economically advantageous plant for the preparation of di-n-butene, for example having a capacity of 200,000 to 800,000 metric t/year, and the same type of plant for preparing RTBE, e.g., having a capacity of 300,000 to 800,000 metric t/year. It would further be desirable to arrange the link between these plants in such a manner that the ratio of n-butene to isobutene can be set in accordance with the desired amounts of RTBE and butene oligomers.

SUMMARY OF THE INVENTION

It is an object of the present invention to provide a process for the coupled production of alkyl tert-butyl ethers and butene oligomers.

It is another object of the present invention to provide a a process for the coupled production of alkyl tert-butyl ethers and butene oligomers, where the ratio of the two reaction products may be controlled by selection of the starting materials.

These objects and others may be accomplished with a process, which comprises:

dehydrogenating a first mixture comprising n-butane and isobutane to produce a second mixture comprising n-butene and isobutene;

etherifying the isobutene in the second mixture with an alcohol to produce an alkyl tert-butyl ether; and oligomerizing the n-butene in the second mixture.

A more complete appreciation of the invention and many of the attendant advantages thereof will be readily obtained as the same becomes better understood by reference to the following detailed description when considered in connection with the accompanying drawing.

BRIEF DESCRIPTION OF THE DRAWING

The FIGURE shows a block diagram of a plant for practicing the process of the present invention.

DETAILED DESCRIPTION OF THE INVENTION

Figure 1:
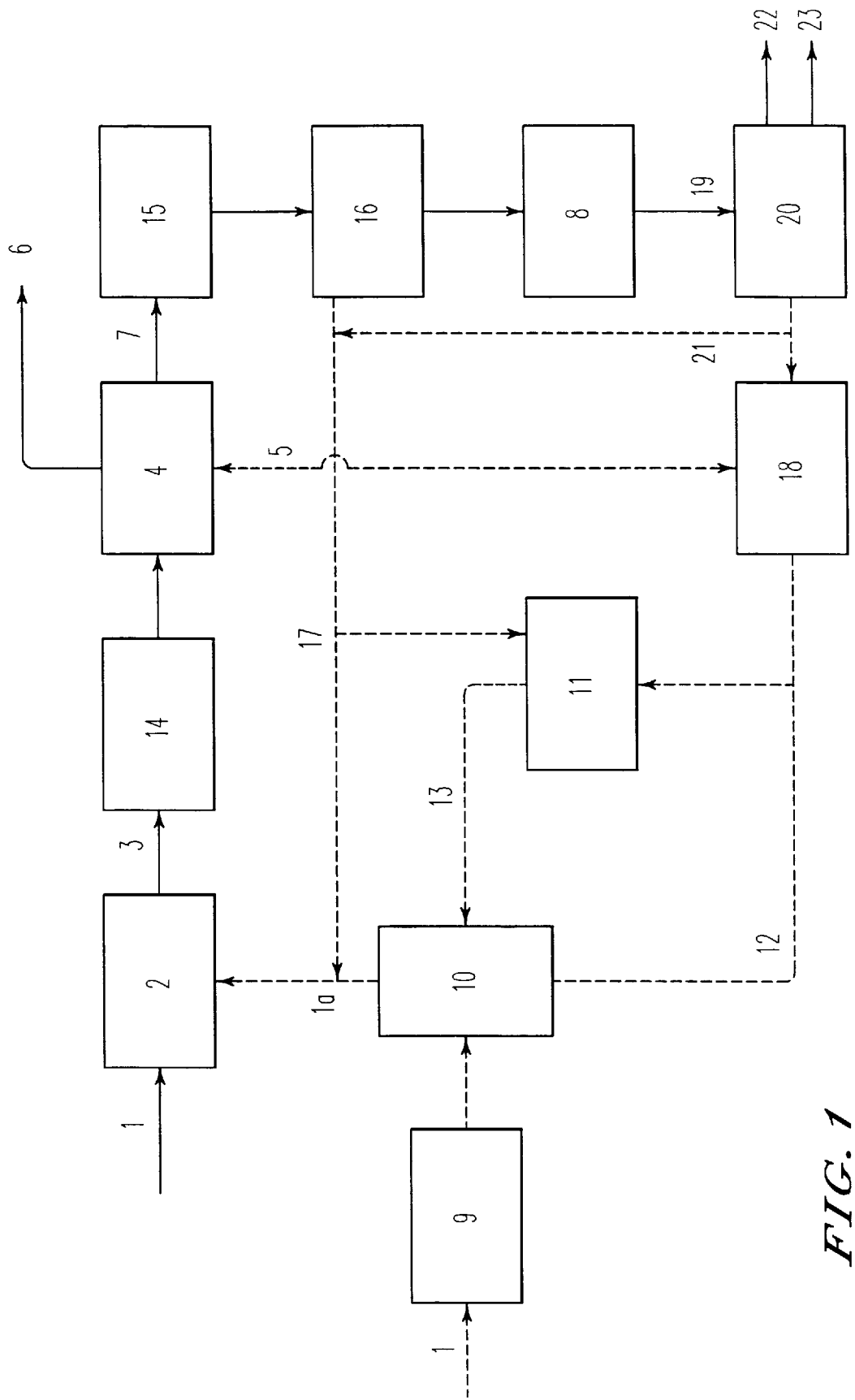

The present invention is a coupled production process in which alkyl tert-butyl ethers and oligomers of butene are produced. The preferred oligomeric product is di-n-butene, but other oligomeric products may also be produced as described below.

In the first step of the present process a mixture containing n-butane and isobutane is dehydrogenated to produce a reaction product mixture containing n-butene and isobutene. A preferred starting mixture is a field butane. The term "field butane" refers to the $C_4$ fraction of the "moist" portions of the natural gas and the gases associated with crude oil, which are separated off in liquid form from the gases by drying and cooling to about −30° C. Low-temperature distillation produces therefrom the field butanes. The composition of the field butanes fluctuates depending on the field generally. Field butanes may contain about 30% isobutane and about 65% n-butane. Other components are generally about 2% $C_{<4}$ hydrocarbons and about 3% $C_{<4}$ hydrocarbons. Field butanes may be used without fractionation as feedstocks in steam crackers or as an additive to motor gasoline. They may be resolved into n-butane and isobutane by fractional distillation. Isobutane is used, for example, to a considerable extent for preparing propylene oxide by cooxidation of propylene and isobutane and as an alkylating agent, by means of which n-butene or isobutene is alkylated to isooctane, which, because of its high octane rating, is valued as an additive to motor gasoline. n-Butane, in contrast, has found fewer such important uses. It serves, for example, as butane gas for heating purposes or is used in comparatively small amounts, for example, for preparing polymers or copolymers or for producing maleic anhydride by atmospheric oxidation. Formerly, n-butane was also dehydrogenated via the n-butene stage to give 1,3-butadiene, but this process has become uneconomic in the interim.

In a preferred embodiment of the process, the field butanes 1, prior to entry into the dehydrogenation stage 2, are subjected to hydrogenation conditions in the hydrogenation stage 9, passed into a separation stage 10 to which an isomerization stage 11 where the ratio of n-butane to isobutane (n/iso ratio) can be adjusted in accordance with the desired ratio of di-n-butene to alkyl tert-butyl ether and the field butane 1a thus altered in its n/iso ratio is passed into the dehydrogenation stage 2.

This preferred embodiment of the invention is distinguished by high flexibility, since the amounts of di-n-butene and RTBE can be varied in accordance with the market requirements, within the limits which are set by the capacities of the di-n-butene plant and the RTBE plant.

Because isobutane is the more sought-after component of field butane, n-butane is isomerized on a large scale to give isobutane (cf., for example, R. A. Pogliano et al., Dehydrogenation-based Ether Production, 1996 Petrochemical Review, DeWitt & Company, Houston, Tex., BUTAMER Process, page 6; and S. T. Bakas, F. Nierlich et al., Production of Ethers from Field Butanes and Refinery Streams. AIChE Summer Meeting, 1990, San Diego, Calif., page 11). It was therefore not part of the technological trend to develop a process which utilizes n-butane as such or even converts isobutane into n-butane in order to prepare more di-n-butene therefrom.

The process according to the invention is carried out in two sequential part-steps (A) preparation of RTBE and (B) preparation of di-n-butene. In principle, the sequence of these part-steps is optional, but it is advantageous to prepare RTBE initially and then di-n-butene, because isobutene is likewise active in oligomerization. The di-isobutene thus formed is, as previously mentioned, less highly branched and thus leads to isononanols having poorer application properties.

(A) Preparation of RTBE

The field butanes 1 or the field butanes which have been altered in composition by isomerization 1a (see section (C)) are passed into the dehydrogenation stage 2, which is an essential feature of the present invention. There, the field butanes are dehydrogenated to give a dehydrogenation mixture 3 containing n-butene and isobutene. The dehydrogenation is a codehydrogenation of n-butane and isobutane. It is remarkable that the dehydrogenation of the field butanes, which are mixtures of components having different dehydrogenation behavior, succeeds so readily. The process conditions substantially correspond to those which are known for n-butane and isobutane. Thus, ST. Bakas, F. Nierlich et al., loc. cit., pages 12 ff., incorporated herein by reference, describe the OLEFLEX process, which is generally suitable for preparing light olefins and by means of which, for example, isobutane can be dehydrogenated to isobutene with a selectivity of 91 to 93%. Further examples are provided by G. C. Sturtevant et al., Oleflex—Selective Production of Light Olefins, 1988 UOP Technology Conference, and EP 0 149 698, both incorporated herein by reference. The dehydrogenation is expediently carried out in the gas phase on fixed-bed or fluidized catalysts, e.g., on chromium(III) oxide, or adavantageously on platinum catalysts having aluminum oxide or zeolites as support. The dehydrogenation preferably takes place at temperatures of 400 to 800° C., more preferably 550 to 650° C. Atmospheric pressure or a slightly elevated pressure up to 3 bar is generally employed. The residence time in the catalyst layer is generally between 1 and 60 minutes, depending on catalyst, temperature and the sought-after degree of conversion. The throughput is generally between 0.6 and 36 kg of n-butane and isobutane (as mixture) per ml of catalyst and hour.

It is preferable to carry out the dehydrogenation only to the point that about 50% of the n-butane and the isobutane remain unchanged in the dehydrogenation mixture 3. Although higher degrees of conversion can be achieved at higher temperatures, cracking reactions which decrease the yield then proceed to an increasing extent, and, as a consequence of coke deposits, decrease the service life of the hydrogenation catalyst. The optimum combinations of reaction conditions which lead to the desired degrees of conversion, such as type of catalyst, temperature and residence time, may be determined without difficulty.

The dehydrogenation mixture 3 generally contains 90 to 95% by weight of $C_4$ hydrocarbons and, in addition, hydrogen, as well as lower- and higher-boiling portions. Preferably, it is subjected to preliminary purification prior to the oligomerization, namely in a first purification stage and in a selective hydrogenation stage 14. In the first purification stage, the $C_4$ fraction and the higher-boiling portions are condensed out of the gas phase. The condensate is distilled under pressure, with cocondensed, dissolved $C_{<4}$ hydrocarbons passing through the head. From the higher-boiling portions, in a further distillation, the saturated and unsaturated $C_4$ hydrocarbons are obtained as main product, which pass into the further process, and the relatively small amount of $C_{<4}$ hydrocarbons are obtained as a residue.

The $C_4$ hydrocarbons generally contain small amounts, e.g., 0.01 to 5 percent by volume, of dienes, such as propadiene and, in particular, 1,3-butadiene. It is preferable to remove these dienes, since, even in markedly lower amounts, they can later damage the catalyst in the oligomerization stage 8. A suitable process is the selective hydrogenation 14, which in addition increases the proportion of the desired n-butene. The selective hydrogenation has been described, for example, by F. Nierlich et al. in Erdol & Kohle, Erdgas, Petrochemie, 1986, pages 73 ff, incorporated herein by reference. It is carried out in liquid phase with completely dissolved hydrogen in stoichiometric amounts. Suitable selective hydrogenation catalysts are, for example, nickel and, in particular, palladium on a support, e.g., 0.3 percent by weight palladium on activated carbon or, preferably, on aluminum oxide. A small amount of carbon monoxide in the ppm range promotes the selectivity of the hydrogenation of the 1,3-butadiene to give the monoolefin and counteracts the formation of polymers, the so-called "green oil", which may inactivate the catalyst. The process generally proceeds at room temperature or elevated temperature up to 60° C. and under elevated pressures which are preferably up to 20 bar. The content of 1,3-butadiene in the dehydrogenation mixture is decreased in this manner to values <1 ppm. Advantageously, the selective hydrogenation is carried out under hydroisomerizing conditions. This simultaneously isomerizes 1-butene to 2-butene, which, in contrast to 1-butene, can be separated from n-butane/isobutane by distillation in the separation stage 16 to be described below. For details of the selective hydrogenation under hydroisomerizing conditions see, e.g., F. Nierlich, Integrated Tert-Butyl Alcohol/Di-n-Butene Production from FCC $C_4$'s, Erdol, Kohle 103 (11), pages 486 ff., 1989, incorporated herein by reference.

Since the dienes may interfere with the later oligomerization, but less so the etherification, the selective hydrogenation stage 14 may also be arranged downstream of the etherification stage 4 in the stream of the residual dehydrogenation mixture 7, upstream or, preferably, downstream of the purification stage 15 to be described below. This arrangement permits, if appropriate, the reactor of the selective hydrogenation stage 14 to be designed to be smaller, because the volume of the residual dehydrogenation mixture 7 after the isobutene has been separated off in the etherification stage 4 is obviously smaller than that of the dehydrogenation mixture 3.

The dehydrogenation mixture 3, if appropriate after preliminary purification and selective hydrogenation, is passed into the etherification stage 4 which is an essential feature of the process according to the invention. There, the isobutene present therein is reacted in a manner known per se with an alkanol 5 (see, for example, methyl tert-butyl ether, Ullmanns Encyclopedia of Industrial Chemistry, Volume A 16, pages 543 ff., VCH Verlagsgesellschaft, Weinheim). The alkanol preferably has 1 to 20 carbon atoms. The more preferred alkanols have 1 to 6 carbon atoms. The alkanol may have the formula R—OH, where R is a $C_{1-20}$ hydrocarbon group. Preferably, the R group is unreactive under the conditions used in the present process. More preferably, R is an alkyl group, i.e., a saturated hydrocarbon group. The alkyl group may have any structure, such as linear, branched, cyclic or combinations thereof. Suitable examples of the alkanol include ethanol, isopropanol, isobutanol and, in particular, methanol.

Since n-butene is considerably less reactive, a selective etherification takes place which consumes virtually only isobutene. The reaction proceeds in the liquid phase or gas-liquid phase, generally at a temperature of 50 to 90° C. and at a pressure which is established at the respective temperature. Preferably, a slight stoichiometric excess of alkanol is employed, which increases the selectivity of the reaction of the isobutene and suppresses its dimerization. The catalyst used is, for example, an acid bentonite or, advantageously, a large-pored acid ion exchanger.

From the etherification stage 4 reaction mixture, the gaseous residual dehydrogenation mixture 7 and the excess alkanol may be separated off from the RTBE 6 formed by distillation. In the case of MTBE, the residual dehydrogenation mixture 7 and methanol form an azeotrope. The azeotrope is washed with water and separated into an aqueous phase and residual dehydrogenation mixture 7. The aqueous phase is worked up to methanol, which is recycled to the etherification, and to water, which is reused for the washing. The residual dehydrogenation mixture 7 passes onto the preparation of di-n-butene.

(B) Preparation of di-n-butene

The starting material for this reaction is the n-butene present in the residual dehydrogenation mixture 7. If no selective hydrogenation 14 has been provided upstream of the etherification stage 4, it may then take place upstream or downstream and, advantageously, downstream of the purification stage 15. The essential component of the latter is a molecular sieve on which other substances harmful for the oligomerization catalyst are removed, which her increases its service life. These harmful substances include oxygen compounds and sulfur compounds. The purification using molecular sieves has been described, for example by F. Nierlich et al. in EP-B1 U395 857, incorporated herein by reference. A molecular sieve having a pore diameter of 4 to 15 angstroms is expediently used, advantageously 7 to 13 angstroms. In many cases, it is expedient for economic reasons to pass the residual dehydrogenation 7 successively over molecular sieves having different pore sizes. The process can be carried out in the gas phase, in liquid phase or in gas-liquid phase. The pressure is correspondingly generally 1 to 200 bar. Room temperature or elevated temperatures up to 200° C. are expediently employed.

The chemical nature of the molecular sieves is less important than their physical properties, i.e., in particular the pore size, The most varied types of molecular sieves can therefore be used, both crystalline, natural aluminum silicates, e.g., sheet lattice silicates, and synthetic molecular sieves, e.g., those having a zeolite structure. Zeolites of the A, X and Y type are obtainable, inter alia, from Bayer AG, Dow Chemical Co., Union Carbide Corporation, Laporte Industries Ltd. and Mobil Oil Co. Also suitable are synthetic molecular sieves which, in addition to aluminum and silicon, further contain atoms introduced by cation exchange, such as gallium, indium or lanthanum, or nickel, cobalt, copper, zinc or silver. In addition, synthetic zeolites are suitable in which, in addition to aluminum and silicon, still other atoms, such as boron or phosphorus, have been incorporated into the lattice by mixed precipitation.

n-Butene from the residual dehydrogenation mixture 7, if appropriate purified by selective hydrogenation 14 and/or treatment with a molecular sieve 15, is advantageously separated off in the separation stage 16 from the other gaseous components (residual gas 1 17), such as isobutane and isobutene which is unreacted in the etherification stage 4, and passed into the oligomerization stage 8 which is an essential part of the process according to the invention. This separation of the residual dehydrogenation mixture 7 upstream of the oligomerization is preferable, because otherwise the oligomerization stage 8 is loaded with unnecessarily high amounts of substance and, in addition, undesirable cooligomers may form from n-butene and isobutene.

The oligomerization is carried out in a manner known per se, such as has been described, for example, by F. Nierlich in Oligomerization for Better Gasoline, Hydrocarbon Processing, 1992 (2), pages 45 ff., or by F. Nierlich et al. in the EP-B 0 395 857, both incorporated herein by reference. The procedure is generally carried out in liquid phase and, as homogeneous catalyst, a system is used, for example, which comprises nickel(II) octoate, ethylaluminum chloride and a free fatty acid (DE-C 28 55 423, incorporated herein by reference), or, preferably, one of the numerous known fixed-bed catalysts or catalysts suspended in the oligomerization mixture based on nickel and silicon is used. The catalysts frequently additionally contain aluminum. Thus, DD-PS 160 037, incorporated herein by reference, describes the preparation of a nickel- and aluminum-containing precipitated catalyst on silicon dioxide as support material. Other catalysts which may be used are obtained by exchanging positively charged particles, such as protons or sodium ions, situated on the surface of the support materials, for nickel ions. This is successful with the most varied support materials, such as amorphous aluminum silicate (R. Espinoza et al., Appl. Kat., 31 (1987), pages 259–266; crystalline aluminum silicate (DE-C 20 29 624); zeolites of the ZSM type (Netherlands Patent 8 500 459); an X zeolite (DE-C 23 47 235); X and Y zeolites (A. Barth et al., Z. Anorg. Allg. Chem. 521, (1985) pages 207–214) and a mordenite (EP-A 0 233 302).

The oligomerization is preferably carried out, depending on the catalyst, at 20 to 200° C. and at pressures from 1 to 100 bar. The reaction time (or contact time) is generally 5 to 60 minutes. The process parameters, in particular the type of catalyst, the temperature and hence the contact time are matched to one another in such a manner that the desired degree of oligomerization is achieved, i.e., predominantly a dimerization. In addition, the reaction should preferably not proceed to full conversion, but conversion rates of 30 to 70% per pass are expediently sought after. The optimum combinations of process parameters may be determined without difficulty.

The residual gas II 21 may be separated off from the oligomerization mixture 19 in the separation stage 20 by distillation. It can then be recycled to the dehydrogenation stage 2 or passed to the isomerization stage 11, if this is present and in operation. Finally, the residual gas II 21, can also be passed into the hydrogenation stage 18, whose function is described below. The alternatives for handling the residual gas II 21 are indicated in the FIGURE by dashed lines. If a catalyst of the liquid catalyst type mentioned was used in the oligomerization stage 8, the residual gases II 21 is preferably purified to protect the dehydrogenation catalyst or the isomerization catalyst. The oligomerization mixture 19 is initially treated with water, in order to extract the catalyst components. The residual gas II 21 which has been separated off may be dried using a suitable molecular sieve, other minor components also being separated off. Polyunsaturated compounds, such as butynes, are then removed by hydrogenation, e.g., on palladium catalysts, and the residual gas II 21 thus purified is finally conducted into the dehydrogenation stage 2 or into the isomerization stage 11. These purifying measures for the residual gas II 21 are not necessary if a fixed-bed oligomerization catalyst is used.

Di-n-butene 22 and trimeric n-butene 23, i.e., isomeric dodecenes, may be further separated off from the remaining liquid phase of the oligomerization mixture 19 in the separation stage 20 by fractional distillation. The main product di-n-butene is directly suitable for preparing nonanols. The dodecenes 23 are a desirable by-product. They can be hydroformylated, the hydroformylation products can be hydrogenated and the tridecanols thus obtained can be ethoxylated, which produces valuable detergent bases.

The residual gas I 17 arising in the separation stage 16 can be recycled to the dehydrogenation stage 2, provided that the field butanes 1 are dehydrogenated directly without changing the n-/iso ratio by isomerization. If an isomerization stage 11 is present and in operation, the residual gas I 17 can be passed directly, or via the hydrogenation stage 18, into the isomerization stage 11. The alternatives for treating the residual gas 1 17 are again depicted in FIG. 1 by dashed lines.

(C) Variation of the amounts of di-n-butene and RTBE

As mentioned above, it is expedient to incorporate an isomerization stage 11 in the process, because by this means the ratio of the amounts of di-n-butene and RTBE (product ratio) can be varied. The possibilities for variation are limited only by the capacities of the di-n-butene and RTBE plants. Taking into account the capital expenditure, both plants are certainly rarely designed to be so large that all of the field butane stream available can be processed in only one of the plants, while the other plant is idle. Nevertheless, the isomerization stage 11 offers the opportunity of reacting flexibly to the requirements of the market within the given limits.

If it is desired to change the present n-/iso ratio of the field butanes 1, they are expediently first passed into a hydrogenation stage 9, if they contain unsaturated compounds. The unsaturated compounds are hydrogenated there and can then no longer damage the catalyst of the isomerization stage 11. The hydrogenation is performed in a manner known per se (see, for example, K. H. Walter et al., in The Hüls Process for Selective Hydrogenation of Butadiene in Crude $C_4$'s, Development and Technical Application, DGKM Meeting, Kassel, November 1993, incorporated herein by reference). The procedure is preferably therefore carried out in liquid phase and, depending on the catalyst, at room temperature or elevated temperature up to 90° C. and at a pressure of 4 to 20 bar, the partial pressure of the hydrogen being 1 to 15 bar. The catalysts which are customary for the hydrogenation of olefins, e.g., 0.3% palladium on aluminum oxide, are used.

The hydrogenated field butanes 1 may be passed into the separation stage 10, whose essential component is an effective column operated at low temperature and/or elevated pressure. If more alkyl tert-butyl ether is to be prepared than corresponds to the isobutane portion of the field butane 1, an amount of n-butane 12 corresponding to the desired product ratio is taken off in the side stream (the $C_{\leq 4}$ hydrocarbons arise as bottom product) and is conducted into the isomerization stage 11. The optional character of this measure is indicated in the FIGURE by a dashed line. In the isomerization stage 11, n-butane is converted into isobutane at the maximum up to equilibrium, which, depending on the temperature, is 40 to 55% n-butane and 60 to 45% isobutane. The isomerization mixture 13 returns to the separation stage 10. As a result, therefore, the dehydrogenation stage 2 is fed with a field butane whose proportion of isobutane is increased with respect to the field butane 1.

If more di-n-butene is to be prepared than corresponds to the n-butane proportion of the field butane 1, the isobutane-rich residual gas I 17 from the separation stage 16 is expediently completely or in part, either directly or via the hydrogenation stage 18, passed into the isomerization stage 11. In this case, the residual gas II 21 is conducted directly into the dehydrogenation stage 2. As a result, the dehydrogenation stage 2 is then fed with a field butane whose proportion of n-butane is increased with respect to the field butane 1.

The isomerization of n-butane and isobutane is a known reaction. The procedure is generally carried out in the gas phase at a temperature of 150 to 230° C., at a pressure of 14 to 30 bar and using a platinum catalyst on aluminum oxide as support, whose selectivity can be further increased by doping with a chlorine compound, such as carbon tetrachloride. A small amount of hydrogen is advantageously added, to counteract a dehydrogenation. The selectivity of the isomerization is high, cracking to form smaller fragments takes place only to a minor extent (approximately 2%) (see, for example, H. W. Grote, Oil and Gas Journal, 56 (13), pages 573 ff. (1958)). The yields of the desired isomer are correspondingly high.

The isomerization mixture may be 13 is recycled to the separation stage 10, from which a field butane 1a having an appropriately altered n-/iso ratio, with respect to the original field butane 1, passes into the dehydrogenation stage 2.

This application is based on German patent application serial No. 196 29 905.5, filed Jul. 24, 1996 and incorporated herein by reference in its entirety.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for preparing alkyl tert-butyl ethers and n-butene oligomers in a desired ratio comprising:

providing a first mixture which is a $C_4$ fraction containing n-butane and isobutane, optionally isomerizing the mixture to adjust the n-butane to isobutane ratio to a desired ratio, when the ratio is not the desired ratio determined by the desired ratio of tert-butyl ether and n-butene oligomers to be produced, to obtain a first mixture altered in its n-butane to isobutane ratio, dehydrogenating the first mixture or said altered first mixture comprising n-butane and isobutane in the desired ratio to produce a second mixture comprising n-butene and isobutene;

etherifying the isobutene in the second mixture with an alcohol to produce an alkyl tert-butyl ether and a residual dehydrogenation mixture containing n-butene; and oligomerizing the n-butene in the residual dehydrogenation mixture.

2. The process of claim 1, wherein the first mixture comprises a field butane.

3. The process of claim 1, further comprising prior to the dehydrogenating step:

isomerizing a mixture comprising n-butane and isobutane to increase the isobutane content of the mixture.

4. The process of claim 3, further comprising prior to the isomerizing step:

hydrogenating the first mixture.

5. The process of claim 1, further comprising prior to the dehydrogenating step:

hydrogenating a mixture comprising n-butane and isobutane.

6. The process of claim 1, wherein the second mixture further comprises dienes, and the process further comprises after the dehydrogenating step and before the etherifying step:

selectively hydrogenating the second mixture to convert the dienes to monoolefins.

7. The process of claim 6, further comprising after the selective hydrogenating step:

contacting the selectively hydrogenated second mixture with at least one molecular sieve.

8. The process of claim 1, further comprising after the dehydrogenating step and before the etherifying step:

contacting the second mixture with at least one molecular sieve.

9. The process of claim 1, wherein the etherification reaction mixture further comprises dienes, and the process further comprises after the etherifying step and before the oligomerizing step:

selectively hydrogenating the etherification reaction mixture to covert the dienes to monoolefins.

10. The process of claim 9, further comprising after the selective hydrogenating step:

contacting the selectively hydrogenated reaction mixture with at least one molecular sieve.

11. The process of claim 1, further comprising after the etherifying step and before the oligomerizing step:

contacting the reaction mixture with at least one molecular sieve.

12. The process of claim 1, further comprising after the etherifying step:

separating the alkyl tert-butyl ether and excess alcohol from the etherification reaction mixture;

separating the n-butene from the residual etherification reaction mixture to produce a residual gas; and incorporating the residual gas into the first mixture used in the dehydrogenating step.

13. The process of claim 3, further comprising after the etherifying step:

separating the alkyl tert-butyl ether and excess alcohol from the etherification reaction mixture;

separating the n-butene from the residual etherification reaction mixture to produce a residual gas; and incorporating the residual gas into the mixture used in the isomerizing step.

14. The process of claim 1, further comprising after the oligomerizing step:

separating a residual gas from the oligomerization reaction mixture; and incorporating the residual gas into the first reaction mixture used in the dehydrogenating step.

15. The process of claim 3, further comprising after the oligomerizing step:

separating a residual gas from the oligomerization reaction mixture; and incorporating the residual gas into the mixture used in the isomerizing step.

16. The process of claim 1, wherein the alcohol has 1 to 20 carbon atoms.

17. The process of claim 1, wherein the alcohol is methanol, ethanol, isopropanol or isobutanol.

18. The process of claim 1, further comprising adding the alkyl tert-butyl ether to a fuel.

19. The process of claim 1, wherein di-n-butene is produced in the oligomerizing step, and the process further comprises:

hydroformylating the di-n-butene; and hydrogenating the hydroformylation reaction product to produce at least one nonanol.

20. The process of claim 1, wherein tri-n-butene is produced in the oligomerizing step, and the process further comprises:

hydroformylating the tri-n-butene;

hydrogenating the hydroformylation reaction product; and ethoxylating the hydrogenation reaction product.

* * * * *